(12) United States Patent
Dow

(10) Patent No.: US 9,744,150 B2
(45) Date of Patent: *Aug. 29, 2017

(54) SUSPENSION CONTAINING MICRONIZED BENZOYL PEROXIDE

(75) Inventor: Gordon Jay Dow, Santa Rosa, CA (US)

(73) Assignee: Dow Pharmaceutical Sciences Inc., Petaluma, CA (US)

(*) Notice: Subject to any disclaimer, the term of this patent is extended or adjusted under 35 U.S.C. 154(b) by 208 days.

This patent is subject to a terminal disclaimer.

(21) Appl. No.: 12/925,214

(22) Filed: Oct. 15, 2010

(65) Prior Publication Data

US 2011/0092562 A1 Apr. 21, 2011

Related U.S. Application Data

(60) Provisional application No. 61/279,468, filed on Oct. 21, 2009.

(51) Int. Cl.
*A61K 31/327* (2006.01)
*A61K 9/10* (2006.01)
*A61K 31/4025* (2006.01)
*A61P 17/10* (2006.01)

(52) U.S. Cl.
CPC ........... *A61K 31/327* (2013.01); *A61K 9/10* (2013.01)

(58) Field of Classification Search
CPC ................. A61K 31/4025; A61K 31/327
USPC ........................................... 514/422
See application file for complete search history.

(56) References Cited

U.S. PATENT DOCUMENTS

| | | | | |
|---|---|---|---|---|
| 3,535,422 A * | 10/1970 | Cox et al. | ...... | 514/714 |
| 4,056,611 A | 11/1977 | Young | | |
| 4,387,107 A | 6/1983 | Klein | | |
| 4,401,835 A * | 8/1983 | Tarasov | ...... | C07C 409/34 252/186.26 |
| 4,671,956 A * | 6/1987 | Bouillon et al. | ...... | 424/59 |
| 4,923,900 A * | 5/1990 | De Villez | ...... | A61K 9/0014 514/714 |
| 5,409,917 A * | 4/1995 | Robinson et al. | ...... | 514/200 |
| 5,446,028 A * | 8/1995 | Klein et al. | ...... | 514/43 |
| 5,733,886 A | 3/1998 | Baroody et al. | | |
| 6,117,843 A * | 9/2000 | Baroody et al. | ...... | 514/24 |
| 7,252,816 B1 * | 8/2007 | Angel et al. | ...... | 424/59 |
| 2009/0191245 A1 | 7/2009 | Fredon | | |
| 2009/0306172 A1 * | 12/2009 | Chang et al. | ...... | 514/422 |
| 2010/0099733 A1 * | 4/2010 | Dow | ...... | 514/422 |
| 2012/0115801 A1 * | 5/2012 | Dow | ...... | 514/28 |

FOREIGN PATENT DOCUMENTS

| | | |
|---|---|---|
| JP | S56-500888 A | 7/1981 |
| WO | 81/00206 A1 | 2/1981 |
| WO | 2008/087354 A2 | 7/2008 |
| WO | 2009/148584 A1 | 12/2009 |

OTHER PUBLICATIONS

Gold, Michael H., "A New, Once-daily, Optimized, Fixed Combination of Clindamycin Phosphate 1.2% and Low-concentration Benzoyl Peroxide 2.5% Gel for the Treatment of Moderate-to-Severe Acne," The Journal of Clinical and Aesthetic Dermatology, May 2009, vol. 2, No. 5, pp. 44-48.

Anonymous: "ACANYA (clindamycin phosphate and benzoyl peroxide) kit [Dow Pharmaceuticals Sciences]", , Oct. 1, 2009 (Oct. 1, 2009), pp. 1-10, XP002696304, Retrieved from the Internet: URL:http://dailymed.nlm.nih.gov/dailymed/lookup.cfm?setid=dabcc73b-e02f-4ebf-85f0-91d33daaf8c5 [retrieved on Apr. 29, 2013].

Anonymous: "Desired Characteristics and Applications of Pharmaceutical suspensions", Jan. 5, 2007 (Jan. 5, 2007), pp. 1-69, XP002696305, Retrieved from the Internet: URL:http://www.pharmainfo.net/free-books/pharmaceutical-suspensionsa-review [retrieved on Apr. 29, 2013].

* cited by examiner

*Primary Examiner* — Sarah Pihonak
*Assistant Examiner* — Jason A Deck
(74) *Attorney, Agent, or Firm* — Kilpatrick Townsend & Stockton LLP

(57) ABSTRACT

Powder containing benzoyl peroxide is readily wetted by contacting the powder with a liquid containing water and one or more water-soluble organic solvents in a concentration sufficient to reduce the surface tension of the liquid to 64 dynes/cm or less. The benzoyl peroxide can then be subjected to a micronization treatment to obtain a suspension containing micronized benzoyl peroxide.

9 Claims, No Drawings

SUSPENSION CONTAINING MICRONIZED BENZOYL PEROXIDE

CROSS-REFERENCE TO RELATED APPLICATIONS

This application claims the benefit of U.S. Provisional Pat. Appl. No. 61/279,468, filed Oct. 21, 2009, which is incorporated herein by reference in its entirety for all purposes.

FIELD OF THE INVENTION

The invention pertains to the field of formulating stable dispersions, including microdispersions and nanodispersions, of benzoyl peroxide.

BACKGROUND OF THE INVENTION

Benzoyl peroxide is used extensively in dermatologic pharmaceutical compositions. Many compositions for the treatment of acne vulgaris and acne rosacea, for example, contain between 2.5% and 10% benzoyl peroxide. The effectiveness of benzoyl peroxide in treating these and other dermatologic conditions is in its usefulness as a keratolytic agent, thereby increasing skin turnover and clearing pores. Benzoyl peroxide additionally has direct antibacterial activity.

A serious difficulty in obtaining stable dispersions of benzoyl peroxide in aqueous fluids is that benzoyl peroxide is a highly hydrophobic organic compound and is not readily wetted by water. This problem has been dealt with by the prior art in one or more ways.

Benzoyl peroxide may be dissolved in an organic solvent, thus avoiding the problem of preparing a stable, homogeneous, cosmetically elegant and efficacious dispersion of benzoyl peroxide for topical administration for treating a skin affliction. Early products containing benzoyl peroxide in solution for topical use were gels in which the benzoyl peroxide was dissolved in an organic solvent such as acetone or a combination of alcohol and acetone. These products proved to be efficacious, however they suffered from several disadvantages including flammability, over-drying the skin, and causing skin irritation in many acne sufferers. More recent developments have used other organic solvents to solubilize benzoyl peroxide. However these compositions do not solve the problem of severe skin irritation in a significant number of subjects due to the problem of bolus delivery of solubilized benzoyl peroxide into the pilo-sebaceous apparatus of the skin.

For these and other reasons, including increased production of degradation products that occurs with solutions, suspensions of benzoyl peroxide are preferred over solutions. Micro-suspensions, which are suspensions containing micronized benzoyl peroxide, are preferred to standard or non-micronized suspensions of benzoyl peroxide for several reasons, including the following exemplary reasons. First, micronized suspensions provide effective delivery of small particles of benzoyl peroxide into the infundibulum of the pilo-sebaceous apparatus, in which they lodge and from which they provide non-bolus delivery of drug into the sebum and pilo-sebaceous tissue. This delivery provides a proper balance of optimal efficacy and reduction of skin irritation reactions. Second, cosmetic elegance and patient acceptance are improved with the smooth, homogeneous gels, creams or lotions containing suspended finely divided or micronized benzoyl peroxide, rather than dissolved benzoyl peroxide which requires significant amounts of organic solvents. Particularly in treating facial conditions of the skin such as acne or acne rosacea, cosmetic elegance is an important factor in obtaining good patient compliance with treatment instructions. For chronic diseases with ongoing topical drug management, good patient compliance is essential in obtaining overall treatment success.

Surfactants are often utilized as wetting agents to help disperse benzoyl peroxide in aqueous fluids and to maintain benzoyl peroxide in suspension during processing and in the finished formulation. Surfactants, however, are often irritating to damaged or diseased skin and, when applied to intact skin repeatedly, surfactants are known to disrupt the normal skin barrier function as evidenced by an increase in transepidermal water loss from the skin. Therefore it is desirable to formulate pharmaceutical compositions, particularly those that will be used daily over extended periods for treating chronic skin conditions, with minimal or no surfactants. In order to facilitate dispersion of benzoyl peroxide and to maintain the dispersion of benzoyl peroxide in suspension, a micronized form of benzoyl peroxide is often utilized, sometimes in conjunction with a surfactant.

Cox, U.S. Pat. No. 3,535,422, discloses a stable emulsion containing benzoyl peroxide. Cox discloses two methods to obtain the emulsion containing benzoyl peroxide in suspension. In a first method, Cox forms an emulsion containing water, a surfactant, and up to 25% of a saturated organic compound emollient. Dry micronized benzoyl peroxide is then blended into this emulsion to obtain the composition. In a second method, utilizing non-micronized benzoyl peroxide, coarse crystals of benzoyl peroxide in the form of a powder packaged wet with water are combined with a previously made emulsion containing all of the components of the composition, including a surfactant and a saturated organic compound emollient. The resulting composition is then milled in order to obtain a composition containing micronized benzoyl peroxide.

Young, U.S. Pat. No. 4,056,611, discloses a single-phase composition containing benzoyl peroxide in suspension. The composition of Young contains an alcoholic solvent, water, and a surfactant as necessary components. Like Cox, Young discloses that the composition may be made by using dry micronized benzoyl peroxide crystals. Preferably, Young utilizes, as does Cox, a wet-packed powder of coarse crystals of benzoyl peroxide, which powder contains about 70% benzoyl peroxide and 30% w/w water. All of the components of the composition are mixed together and then this mixture is milled to obtain a composition containing micronized benzoyl peroxide in suspension. Young further discloses that the compositions may advantageously contain a suspending agent to maintain the benzoyl peroxide particles in suspension and a viscosity building (gelling) agent.

The Cox and Young methods and compositions contain several disadvantages pertaining to compositions containing benzoyl peroxide. In both Cox and Young, surfactants are utilized, which are often irritating to damaged or diseased skin. Further, both Cox and Young disclose combining together all constituents of their compositions containing coarse, non-micronized benzoyl peroxide to form a mixture and then milling this mixture to obtain a composition containing micronized benzoyl peroxide. Although Young discloses that a gelling agent may be combined in the composition, it is well known that the mechanical milling forces used to micronize benzoyl peroxide will likewise tend to disrupt the polymers utilized as gelling agents. Thus, the milling process results in a reduction of the ability of the gelling agents to provide the viscosity that is desired.

Klein, U.S. Pat. No. 4,387,107, discloses gel compositions containing benzoyl peroxide. Klein avoids the problem of milling a composition containing benzoyl peroxide by using benzoyl peroxide that is pre-micronized prior to combining with the remaining ingredients. In order to make the composition of Klein, water is combined with a gelling agent to make a first mixture. To this mixture is optionally added an alcohol vehicle and other components such as a perfume and other therapeutic agents such as methyl salicylate. Finally, a second mixture containing micronized benzoyl peroxide, a surfactant, and water is added to the first mixture to obtain the composition. Because micronized benzoyl peroxide is used, there is no need to mechanically mill the composition. Thus, the polymeric gelling agents are not disrupted. However, the method of Klein requires the use of pre-micronized benzoyl peroxide and the presence of a surfactant.

The use of micronized benzoyl peroxide, as disclosed in Klein, provides advantages, particularly regarding the formation of semi-solid compositions containing one or more polymeric gelling agents. Micronized, as opposed to non-micronized benzoyl peroxide, is more readily suspended in a hydrophilic fluid and such suspensions are more physically stable than are similar suspensions made with non-micronized benzoyl peroxide. However, micronized benzoyl peroxide, particularly as pharmaceutical grade material, is often difficult to obtain and, when it is obtainable, micronized benzoyl peroxide is expensive.

It would, therefore, be advantageous to be able to purchase non-micronized benzoyl peroxide, which is readily available and is much less expensive than micronized benzoyl peroxide, and to then be able to micronize the benzoyl peroxide for use in manufacturing pharmaceutical formulations.

As disclosed in both the Cox and Young patents, benzoyl peroxide, in solid crystalline form, is stable at room temperature but is flammable and capable of exploding when subjected to temperatures associated with grinding. Consequently, dry milling of benzoyl peroxide is not preferred. Rather, it is preferred to wet-mill benzoyl peroxide in order to obtain benzoyl peroxide in a micronized form. Benzoyl peroxide in the presence of water, which is utilized in the preferred wet milling processes, is much safer to process as the risk of fire and explosion is minimized.

Baroody, U.S. Pat. No. 6,117,843, discloses in Example 8 the making of a benzoyl peroxide suspension in an aqueous medium. According to the method of Baroody, propylene glycol was dissolved in water and then a carboxy vinyl polymer was added, followed by addition of a neutralizing agent to obtain a dispersion having a desired pH. Then, benzoyl peroxide was levigated with a portion of the carboxy vinyl polymer dispersion and passed through a homogenizer until the average particle size was less than 25 microns in diameter. Finally, this benzoyl peroxide dispersion was combined with additional water and mixed until a homogenous suspension was obtained.

The method disclosed in Baroody utilizes polymer in order to build significant viscosity and thereby facilitate a high energy mechanical process of wetting. The aqueous fluid to which the BPO is added is a gel. The gel provides thickening, suspending, and coating properties for the BPO powder, which is levigated in a portion of the carboxy vinyl polymer dispersion in order to make the suspension. There are several disadvantages associated with the method of Baroody. One such disadvantage is that the milling process that is part of the method may lead to breakdown of the polymer that is within the dispersion with subsequent loss of gel viscosity and/or stability. Another disadvantage with the Baroody method is that levigation is a manual mechanical laboratory procedure and is not readily translatable to scaled-up commercial manufacture.

One difficulty encountered in wet-milling benzoyl peroxide, as mentioned above, is that benzoyl peroxide is highly hydrophobic and resists wetting with water. Further, the strong attractive forces between benzoyl peroxide particles create a problem of aggregation which may compromise both the manufacturing process and the quality of the final pharmaceutical formulation. Surfactants have been utilized for this purpose and to maintain a stable-non-agglomerated micro-suspension of benzoyl peroxide, as disclosed in each of Cox, Young, and Klein patents, but surfactants are not preferred due to their tendency to irritate sensitive, damaged, or diseased skin. Therefore, a method in which benzoyl peroxide may be readily wetted, and preferably placed into a stable suspension, in a hydrophilic or aqueous fluid, and preferably without the use of surfactants, would be of great benefit.

DESCRIPTION OF THE INVENTION

It has been unexpectedly discovered that a benzoyl peroxide powder is readily wetted, and a benzoyl peroxide suspension with minimal or no aggregation may be obtained, by combining the benzoyl peroxide, with or without mechanical agitation, with a wetting fluid, preferably aqueous-based, in which is dissolved a water-soluble organic solvent at a concentration that is sufficient to decrease the surface tension of the wetting fluid to about 64 dynes/cm or less. It has further been discovered that this wetting may be obtained without the use of wetting agents, such as a surfactant.

As used herein, the term "benzoyl peroxide powder" means any particulate form of benzoyl peroxide. Examples of such particulate forms include granules, crystals, and amorphous powder, whether coarse, fine, micronized, or ultrafine such as a nanoparticulate powder. An example of a benzoyl peroxide powder, as discussed below, is hydrous benzoyl peroxide.

As used herein, the term "powder containing benzoyl peroxide" refers to a powder containing benzoyl peroxide and optionally one or more materials other than benzoyl peroxide. For example, a powder containing benzoyl peroxide may contain particles of benzoyl peroxide and one or more other materials, such as particles, wherein the concentration of materials other than benzoyl peroxide in the powder is 50% w/w or less. A powder containing benzoyl peroxide may contain a concentration of benzoyl peroxide between 50% and 100%, for example between 50% and 60%, between 60% and 70%, between 70% and 80%, between 80% and 90%, or between 90% and 100%.

As used herein, the term "non-micronized," when used in reference to a benzoyl peroxide powder, means a powder in which the average benzoyl peroxide particle is 50 microns or greater in size. Conversely, the term "micronized," when used in reference to a benzoyl peroxide powder, means a powder in which the average benzoyl peroxide particle is less than 50 microns and greater than or equal to 1.0 micron in average size. The terms "nanosize," "nanoparticle," "nanosuspension," "nanodispersion," or "nanoparticulate" mean, in reference to benzoyl peroxide, a powder in which the benzoyl peroxide particles have an average diameter of 1 to 999 nanometers.

As used herein, the term "wetting" refers to the spreading of a fluid over and through a powder, displacing air adsorbed thereto, so that the particles of the powder are individually and discretely encompassed within the fluid. As is known in the art, a powder is considered to be wetted when almost all, such as about 80%+/−10% based on visual inspection and estimation, of the particles are encompassed within the fluid. For example, contacting a powder with a suitable wetting fluid results in what is referred to as complete wetting even though a minority of the particles, typically less than about 20%+/−10% of the particles, does not become wetted.

As used herein, the term "mechanical agitation" refers to the application of kinetic energy to a powder mixture in contact with a liquid in order to facilitate wetting of the powder mixture within the liquid. Examples of mechanical agitation include but are not limited to milling including ball mills and media mills, homogenizing, mixing, stirring, shearing, shaking, or blending. Other examples include sonication and vortexing.

As used herein, the term "aqueous gel" with regards to a pharmaceutical dosage form for topical application means a single phase semi-solid pharmaceutical dosage form comprising a carrier or carrier system that is gelled with a thickening agent such as a polymer wherein the majority of the carrier or carrier system is water, that is 50% w/w or more.

As used herein, the term "agglomeration" means a strong physical attraction between small solid particles, such that a multiplicity of the particles are aggregated into a single larger mass that appears as a single particle. Kinetic or other energy may be applied to de-agglomerate the particle mass.

As used herein, the term "surface tension" refers to the force required to increase the unit area of a surface of a liquid or of an interface between two liquids or between a liquid and a gas, generally stated in units of dynes/cm. Surface tensions described herein are measured by the Du Noüy ring method utilizing an EasyDyne tensiometer model K20 marketed by Krüss USA, Matthews, N.C.

In one embodiment, the invention is a method to obtain a wetted powder containing benzoyl peroxide. According to the method of the invention, the powder is placed in contact with a liquid containing water and a water-soluble organic solvent. The solvent is present in the liquid at a concentration sufficient to obtain a surface tension of less than 64 dynes/cm at room temperature, compared to the 72 dynes/cm surface tension of pure water at room temperature (25° C.). In a preferred embodiment, the solvent is present in the liquid, such as water, at a concentration sufficient to lower the surface tension to less than 62 dynes/cm. In a more preferred embodiment, the solvent is present in the liquid at a concentration sufficient to depress the surface tension to less than 61 dynes/cm. In a most preferred embodiment, the solvent is present in the liquid at a concentration sufficient to reduce the surface tension to less than 60 dynes/cm. For example, the solvent may be present in the liquid at a concentration sufficient to reduce the surface tension to between 55 and 60 dynes/cm or even to between 50 and 55 dynes/cm or less.

In the description that follows, the method is described with reference to reducing the surface tension to less than 64 dynes/cm. As disclosed in the preceding paragraph, preferably, the surface tension is decreased to values even further, such as between 50 and 62 dynes/cm or lower.

Non-micronized benzoyl peroxide is available as Hydrous Benzoyl Peroxide, USP, which is sometimes erroneously referred to as "wet" benzoyl peroxide. Hydrous Benzoyl Peroxide, USP contains not less than 65.0% and not more than 82.0% benzoyl peroxide, with an average of about 74% benzoyl peroxide and 26% water, in order to reduce flammability and sensitivity to explosion. The benzoyl peroxide in Hydrous Benzoyl Peroxide, USP is not wetted, as this term is used in the art. Hydrous Benzoyl Peroxide, USP is not a paste and the benzoyl peroxide in Hydrous Benzoyl Peroxide, USP is in a crystalline or granular state and behaves as a freely flowing powder. The water does not make the core or the inside of the benzoyl peroxide powder wet. Thus, commercially available "wet" benzoyl peroxide (i.e., Hydrous Benzoyl Peroxide, USP) is not wetted.

The benzoyl peroxide in the powder may be micronized or nanoparticulate, or may be non-micronized and, therefore, the description herein pertaining to non-micronized powders will be understood to be applicable also to micronized and nanoparticulate powders. Micronized benzoyl peroxide powders are sometimes commercially available as a wetted powder containing benzoyl peroxide and water. An example of wetted benzoyl peroxide powders are those marketed under the brand name BENOX® (Syrgis Performance Initiators, Inc., Helena, Ark.). Because powders containing micronized benzoyl peroxide are already wetted, such powders are not applicable to the wetting embodiment of the present invention. However, the use of wetted powders containing micronized benzoyl peroxide may be applicable to other embodiments of the invention discussed below.

In accordance with the method of the invention for obtaining a wetted benzoyl peroxide powder, a powder containing benzoyl peroxide is placed in contact with a suitable wetting fluid, which wetting fluid contains water and one or more water-soluble organic solvents having a combined concentration that is sufficient to obtain a desired surface tension of the wetting fluid. Preferably, the wetting fluid is free of surfactants. The powder and the wetting fluid are permitted to remain in contact with one another for a time sufficient for the benzoyl peroxide to become wetted by the wetting fluid. If desired, or if necessary, the powder and the wetting fluid may be mechanically agitated to facilitate or to hasten or to complete wetting.

The organic solvent that is suitable for the method of the invention is one that is "very soluble", "freely soluble", or "soluble" in water as these terms are defined in the U.S. Pat. No. 23rd Ed. as shown in Table 1.

TABLE 1

| Solubility in water | Parts of water required to dissolve 1 part of organic solvent |
|---|---|
| Very Soluble | <1 |
| Freely Soluble | 1-10 |
| Soluble | 10-30 |
| Sparingly Soluble | 30-100 |
| Slightly Soluble | 100-1000 |
| Very Slightly Soluble | 1000-10,000 |
| Practically Insoluble or Insoluble | >10,000 |

Preferably, but not necessarily, the organic solvent is miscible in water. Examples of organic solvents that are miscible in water and which are suitable for the method of the invention include $C_{1-6}$ alkanols, such as methanol, ethanol, n-propanol, isopropanol, n-butanol, sec-butanol, tert-butanol, n-pentanol, cyclopentanol and cyclohexanol; linear amides, such as dimethylformamide or dimethylacetamide; ketones and ketone-alcohols, such as acetone, methyl ethyl ketone, cyclohexanone and diacetone alcohol; water-miscible ethers, such as tetrahydrofuran and dioxane; diols, preferably diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, such as diethylene glycol, triethylene glycol, polyethylene glycol and polypropylene glycol; triols such as 1,2,6-hexanetriol; mono-$C_{1-4}$-alkyl ethers of diols, such as mono-$C_{1-4}$-alkyl ethers of diols having 2 to 12 carbon atoms, such as 2-methoxyethanol, 2-(2-methoxyethoxy)ethanol, 2-(2-ethoxyethoxy)-ethanol, 2-[2-(2-methoxyethoxy)ethoxy] ethanol, 2-[2-(2-ethoxyethoxy)-ethoxy]-ethanol and ethylene glycol monoallylether; cyclic amides, preferably 2-pyrrolidone, N-methyl-2-pyrrolidone, N-ethyl-2-pyrrolidone, caprolactam and 1,3-dimethylimidazolidone; sugar esters such as dimethyl isosorbide; cyclic esters such as caprolactone; and sulfoxides, such as dimethyl sulfoxide and sulfolane.

In addition, the solvent that is suitable for the method of the invention is capable of being dissolved in water at a concentration that is sufficient to reduce the surface tension of the water/solvent combination to less than about 64 dynes/cm at room temperature. The surface tension of water varies with changes in temperature as shown below in Table 2.

TABLE 2

| Temperature (° C.) | Surface Tension of Water (dynes/cm) |
|---|---|
| 0 | 75.6 |
| 5 | 74.9 |
| 10 | 74.2 |
| 15 | 73.5 |
| 20 | 72.8 |
| 25 | 72.0 |
| 30 | 71.2 |
| 40 | 69.6 |
| 50 | 67.9 |
| 60 | 66.2 |
| 70 | 64.4 |
| 80 | 62.6 |
| 100 | 58.9 |

Preferably, the method of the invention to wet a benzoyl peroxide powder is performed at about room temperature, that is between 20° and 30° C. Less preferably, the method of the invention is performed at a temperature below room temperature, that is between 0° and 20°. Also less preferably, the method of the invention is performed at a temperature above room temperature, that is between 30° and 50° C. Even less preferable, the method of the invention may be performed at high temperatures of between 50° and about 95° C. Because one of the advantages of the present invention is the lack of necessity to apply heat, it is preferable to perform the method of the invention at room temperature or below. However, if heat is applied and the temperature is elevated above room temperature, the optimum surface tension for wetting may be slightly higher than 64 dyne/cm. Temperatures above 50° C. are not preferred because of potential problems involving drug instability, lability of solvents, evaporative losses, and flammability.

The wetting fluid may contain, in addition to the one or more water soluble organic solvents, additional components that may be additional solvents. Such additional components are preferably liquid at the temperature at which the wetting process is performed and are preferably soluble in the water soluble organic solvents that are utilized. Optionally the wetting fluid may contain dissolved solutes such as additional wetting agents, film-forming agents, or de-aggregation agents.

Unless the dosage form is a cream or a lotion, or other form that requires an emulsifier, it is preferred not to include a surfactant during the wetting of the benzoyl peroxide powder or in the final dosage form. When a gelling agent is required in the final dosage form, such as in a gel, it is preferred that the gelling agent is added after the wetting of the benzoyl peroxide powder.

It has been surprisingly discovered that a wetting fluid that is a liquid containing water and one or more water soluble organic solvents as described above is capable of wetting a powder containing benzoyl peroxide. The concentration of the water miscible organic solvent or solvents in the wetting fluid will vary depending on factors such as the particular solvent or solvents used, and on the relative amounts of benzoyl peroxide powder and wetting fluid used. Generally, the concentration of the water soluble organic solvent in the wetting fluid is between 1% and 100% w/w. Preferably, the concentration is between about 5% and 95%, more preferably between about 10% and 90%, and most preferably between about 15% and 85%. The term "about" in the preceding sentence is intended to mean an amount that is rounded to be the amount stated. Thus, about 5% means 4.5% to 5.5%, about 10% means 9.5% to 10.5%, and about 15% means 14.5% to 15.5%. The powder and the wetting fluid may be mechanically agitated to facilitate, to hasten, or to complete wetting.

In another embodiment, the invention is a wetted benzoyl peroxide powder that is in combination with a liquid containing water and one or more water soluble organic solvents as described above, wherein the concentration of the water soluble organic solvent in the liquid is sufficient to obtain a surface tension of less than 64 dynes/cm at room temperature as described above.

In another embodiment, the invention is a wetted benzoyl peroxide powder that is in combination with a liquid containing one or more water soluble organic solvents as disclosed above, wherein the concentration of the organic solvent or solvents in the liquid is sufficient to produce a surface tension less than 64 dynes/cm at room temperature.

In another embodiment, the invention is a wetted benzoyl peroxide powder that is in combination with a liquid containing one or more water soluble organic solvents as disclosed above, wherein the concentration of the organic solvent or solvents in the liquid is sufficient to obtain a surface tension less than 64 dynes/cm at room temperature and result in wetting of the benzoyl peroxide powder, thereby reducing and controlling agglomeration of the benzoyl peroxide particles, whether micronized, non-micronized, nanoparticulate or other form of powder, during the manufacturing process of a topical drug product or component thereof.

In another embodiment, the invention is a method for preparing micronized benzoyl peroxide, such as for use in making a topical pharmaceutical formulation containing benzoyl peroxide as an active ingredient. According to this embodiment of the invention, a wetting fluid containing water and a water soluble organic solvent at a concentration sufficient to reduce the surface tension to less than 64 dynes/cm at room temperature is combined with a powder containing non-micronized benzoyl peroxide. The wetting fluid is permitted to wet the majority of the benzoyl peroxide particles in the powder. The wetted benzoyl peroxide is then subjected to an appropriate micronization procedure to obtain micronized benzoyl peroxide. Preferably, the concentration of wetted benzoyl peroxide in the wetting fluid that is to be micronized is between 1% and 95%, such as between 5% and 80%, and most preferably between 15% and 50%.

In another embodiment, the invention is a suspension of benzoyl peroxide. According to this embodiment, the suspension is a single phase composition containing benzoyl peroxide at a concentration of between 1% and 30% w/w, preferably 10% or less, and most preferably 5% or less. Preferred concentrations of benzoyl peroxide include about 1%, 1.25% 1.5%, 1.75%, 2%, 2.25%, 2.5%, 2.75%, 3%, 3.25%, 3.5%, 3.75%, 4%, 4.25%, 4.5%, 4.75%, and 5%. The benzoyl peroxide is suspended in a suspending fluid that contains one or more water soluble organic solvents at a concentration sufficient to reduce the surface tension of the fluid to less than 64 dynes/cm at room temperature. The suspending fluid may contain only the one or more organic solvents. Alternatively, the suspending fluid may contain one or more vehicle fluids that are other than a water soluble organic solvent that is capable of reducing the surface tension to less than 64 dynes/cm at room temperature.

It is preferred that the suspending fluid contains only one or more of the above-described water soluble organic solvents in addition to water. If a vehicle fluid other than a water soluble organic solvent that is capable of reducing the surface tension of water to less than 64 dynes/cm at room temperature is utilized, such vehicle fluid should be pharmaceutically acceptable and miscible with the one or more of the water soluble organic solvents used. Further, the concentration of the one or more water soluble organic solvent that is capable of reducing the surface tension to less than 64 dynes/cm at room temperature in the suspending fluid should be that which is sufficient, in the absence of the vehicle fluid that is other than such water soluble organic solvent, to wet a benzoyl peroxide powder therewith combined.

The benzoyl peroxide in the suspension may be micronized or nanoparticulate, or may be non-micronized. If the benzoyl peroxide is non-micronized, the suspension may be treated by a process by which the benzoyl peroxide in the suspension becomes micronized or nanoparticulate. Suitable micronization processes include milling, grinding, crushing, cutting, impinging, cavitating, homogenizing, and shearing the suspension. Suitable processes to produce nanoparticles of the benzoyl peroxide powder include but are not limited to ball milling and media milling of the suspension made as described herein. Milling processes using grinding media with or without surfactants in order to make nanoparticle formulations are disclosed in Liversidge, U.S. Pat. No. 5,399,363, which is incorporated herein by reference.

Non-micronized benzoyl peroxide, when wetted and suspended in accordance with the method of the invention, has a very low tendency to agglomerate or aggregate on the liquid surface and, therefore, there is little or no problem of benzoyl peroxide particles becoming stuck in the small orifices of the micronizing equipment such as a Gaulin mill (Delavan, Wis.). Benzoyl peroxide particles that have been wetted in accordance with the method of the invention and then micronized remain in stable suspension and do not agglomerate or aggregate on the liquid surface to a significant extent prior to being incorporated into a pharmaceutical formulation such as a gel, cream, lotion, or foam. The stable suspension of non-micronized, micronized, or nanoparticulate benzoyl peroxide obtained according to the invention thus results in good pharmaceutical homogeneity and optimal non-bolus delivery into the skin, particularly the pilosebaceous apparatus, thus minimizing irritation potential without compromising efficacy.

In another embodiment, the invention is a method for preparing micronized benzoyl peroxide, such as for use in making a topical pharmaceutical formulation containing benzoyl peroxide as an active ingredient. In accordance with this method, a benzoyl peroxide powder is wetted and in suspension as described above, and the benzoyl peroxide suspension is then subjected to appropriate micronization treatment to obtain a suspension containing micronized benzoyl peroxide.

In another embodiment, the invention is a suspension containing micronized benzoyl peroxide, which benzoyl peroxide has been micronized according to the method described above. The micronization process and suspension of benzoyl peroxide of the invention are useful in formulating topical pharmaceutical products containing benzoyl peroxide as an active ingredient, especially topical products that are semi-solid dosage forms. The methods of the invention maintain the dispersed micronized benzoyl peroxide in a stable non-agglomerated and non-aggregated state for optimal pharmaceutical acceptability without the need to include a "shake well before using" label in lotions and other pourable topical dosage forms and for optimal drug delivery.

In another embodiment, the invention is a pharmaceutical formulation containing benzoyl peroxide in suspension in a liquid containing one or more water-soluble organic solvents that is, or are in combination, capable of reducing the surface tension of an aqueous fluid to less than 64 dynes/cm at room temperature, wherein the concentration of the water-soluble organic solvents together with the water in the pharmaceutical formulation is sufficient to wet a powder containing benzoyl peroxide at a concentration of the benzoyl peroxide present in the formulation in the absence of all other liquid components of the formulation. Preferably, the benzoyl peroxide is micronized or nanoparticulate. Preferably, the benzoyl peroxide has been micronized or made into nano-sized particles according to the present invention. If desired, the pharmaceutical formulation may contain one or more additional vehicle fluids or solutes, as described above. The pharmaceutical formulation may further contain excipients commonly utilized in pharmaceutical formulations, such as humectants, emollients, pH stabilizing agents, thickening agents, gelling agents, suspending agents, chelating agents, film forming agents, preservatives, anti-oxidants, and other active pharmaceutical ingredients.

The concentration of benzoyl peroxide in the pharmaceutical formulation is preferably between 1% and 10% w/w, with a preferred concentration being between 2% to 5%. If desired, an additional agent that is useful in the treatment of dermatologic disorders such as acne vulgaris or acne rosacea may be included in the formulation. Preferably, the additional anti-acne compound is soluble in the solvent or multiplicity of solvents and so is dissolved in the formulation.

One such preferred anti-acne compound is an antibiotic. Preferred antibiotics include those of the macrolide family of antibiotics such as erythromycin, azithromycin, clarithromycin, tilmicosin, and tylosin, and those of the lincomycin family of antibiotics such as clindamycin and lincomycin. A particularly preferred antibiotic to be used in combination with benzoyl peroxide in the formulation of the invention is clindamycin, such as clindamycin hydrochloride or clindamycin phosphate. Additional topical anti-acne active ingredients that may be contained in the formulation of the invention, either with or without the inclusion of an antibiotic, include salicylic acid, azelaic acid, sulfur, sodium sulfacetamide, resorcinol, alpha-hydroxy acids such as glycolic acid, niacinamide, urea, and retinoids such as tretinoin, adapalene, and tazarotene.

The additional anti-acne compound, if present in the formulation of the invention, is preferably present in a concentration in which there is a demonstrable anti-acne effect in the absence of benzoyl peroxide. For example, if clindamycin is present in the formulation of the invention, the concentration of the clindamycin is preferred to be at least 0.5%, such as 1%. Concentrations of clindamycin lower than 0.5% or higher than 1%, such as 2.5% to 5.0% or higher, may be utilized in the formulation.

It is preferred, although not required, that the formulation be in the form of a gel, preferably an aqueous gel. Accordingly, the formulation of the invention may contain a gelling or thickening agent. Any gelling agent that is water-dispersible, is suitable for use on epithelial tissue such as skin, and forms an aqueous gel of substantially uniform consistency, is suitable for use in the composition of the invention. One preferred gelling agent is hydroxypropylcellulose, such as that sold under the tradename KLUCEL® (Hercules Incorporated, Wilmington, Del., USA). Another preferred gelling agent is hydroxyethylcellulose, such as that sold under the tradename NATROSOL® (Hercules Incorporated). Other suitable gelling agents include carboxyvinyl polymers, also known as carbomers, such as are sold under the tradename CARBOPOL® 934, 940, 941, 980, and 981 (B.F. Goodrich Co., Akron, Ohio, USA), ETD 2020™, and ULTREZ® (Noveon, Inc., Cleveland, Ohio, USA). Additional suitable gelling agents are polyvinyl alcohol, polyethylene oxides, propylene glycol alginates, methylcellulose, hydroxypropylmethylcellulose and natural polymeric gums such as xanthan, and carrageenan. The concentration of gelling agent in the composition may be varied depending on several factors, including the desired viscosity of the gel composition. For example, a gel may be pourable and dispensed from a bottle, such as a plastic squeeze bottle, or it may be more viscous such that it is preferably dispensed from a collapsible tube, a pump package system, or wide mouth jar. When forming a gel or other dosage form containing a gelling agent, it is preferred that the gelling agent is added to a benzoyl peroxide suspension after the benzoyl peroxide powder is wetted and after any particle size reduction steps are utilized to make a micronized or nanoparticulate suspension.

A further embodiment of the invention is a method for making a semi-solid pharmaceutical dosage form, such as a gel, containing micronized or nanoparticulate benzoyl peroxide including the following steps: 1) forming a suspension of benzoyl peroxide particles in a liquid containing one or more water-soluble organic solvents that is, or are in combination, capable of reducing the surface tension of a water-based fluid to less than 64 dynes/cm at room temperature, wherein the concentration of the water-soluble organic solvents together with the water in the pharmaceutical formulation is sufficient to wet a powder containing benzoyl peroxide at a concentration of the benzoyl peroxide present in the formulation in the absence of all other liquid components of the formulation.

If desired, the formulation of the invention may further include additional pharmaceutically acceptable excipients typically used in formulations and known to those skilled in the art. Such excipients include, for example, humectants, emollients, pH stabilizing agents, chelating agents, film formers, penetration enhancers, preservatives, and anti-oxidants.

The semi-solid dosage form of the pharmaceutical formulation of the invention may also be in the form of an emulsion, such as a cream or lotion. Preferably, such creams or lotions are formulated without low molecular weight surfactants due to the tendency of such surfactants to be irritating to the skin or to impair the skin barrier function. Thus, it is preferred that the cream or lotion formulations of the invention are made with high molecular weight polymeric emulsifiers which do not exhibit such detrimental effects on skin, such as disclosed in Dow, U.S. Pat. No. 7,368,122, or with low levels of mild high molecular weight emulsifiers such as poloxamers.

The invention is further described in the following non-limiting examples. In the examples that follow, the invention is illustrated primarily with organic solvents that are miscible with water. However, it is understood that the examples are illustrative and that the invention may be practiced with water soluble solvents that are not miscible with water, as described above.

EXAMPLE 1

Wetting of a Benzoyl Peroxide Powder Utilizing Various Water Soluble Organic Solvents A benzoyl peroxide wettability study was conducted as follows. 1.5 grams of a benzoyl peroxide powder (PERKADOX® API Powder, AkzoNobel, Inc., Chicago, Ill.) was spread on the surface of each of four test fluids contained in glass beakers having about a 5 cm diameter, containing either 30 ml of purified water having a surface tension of 72.0 dynes/cm (Sample A), 30 ml of a fluid composed of 2.5% ethanol (200 proof, Spectrum Chemicals, Gardena, Calif.) and 97.5% purified water having a surface tension of 62.0 dynes/cm (Sample B1), 30 ml of a fluid composed of 7.5% ethanol and 92.5% purified water having a surface tension of 51.4 dynes/cm (Sample B2), 30 ml of a fluid composed of 5% polyethylene glycol 200 NF (PEG 200) (Alfa Aesar, Ward Hill, Mass.) and 95% purified water having a surface tension of 61.1 dynes/cm (Sample C1), 30 ml of a fluid composed of 20% polyethylene glycol 200 and 80% purified water having a surface tension of 51.9 dynes/cm (Sample C2), 30 ml of a fluid composed of 5% dimethyl isosorbide (DMI) (Croda USA, Edison, N.J.) and 95% purified water having a surface tension of 60.9 dynes/cm (Sample D1), 30 ml of a fluid composed of 20% dimethyl isosorbide and 80% purified water having a surface tension of 50.1 dynes/cm (Sample D2), 30 ml of a fluid composed of 5% ethoxydiglycol NF (TRANSCUTOL® GattefosséUSA, Paramus, N.J.) and 95% purified water having a surface tension of 56.8 dynes/cm (Sample E1), 30 ml of a fluid composed of 12.5% ethoxydiglycol and 87.5% purified water having a surface tension of 50.4 dynes/cm (Sample E2), 30 ml of a fluid composed of 2.5% propylene carbonate (Spectrum Chemicals, Gardena Calif.) and 97.5% purified water having a surface tension of 63.8 dynes/cm (Sample F1), 30 ml of a fluid composed of 7.5% propylene carbonate and 92.5% purified water having a surface tension of 49.6 dynes/cm (Sample F2), 30 ml of a fluid composed of 12.5% propylene glycol and 87.5% purified water having a surface tension of 59.7 dynes/cm (Sample G1), 30 ml of a fluid composed of 30% propylene glycol and 70% purified water having a surface tension of 50.5 dynes/cm (Sample G2), and 30 ml of a fluid composed of 1% polypropylene glycol and 99% purified water having a surface tension of 50.3 dynes/cm (Sample H).

At the bottom of each beaker was a 12 mm×8 mm magnetic stir bar. Each of the fluids, with the benzoyl peroxide powder on the surface, was stirred at 1200 rpm. After 5 and 10 minutes of stirring at room temperature, the samples were visually inspected for the degree of wetting of the benzoyl peroxide. It was determined that the wetting of the benzoyl peroxide in Sample A was poor, with little or no visual evidence of wetting. The wetting of the benzoyl peroxide in each of Samples A to H was determined to be good, with visual evidence of wetting of at least 80% and, in many cases, of at least 90% of the benzoyl peroxide powder.

The data of Example 1 is illustrated in Table 3 below.

TABLE 3

| Sample | Solvent | Concentration of Solvent % w/w in Water | Surface Tension dynes/cm | Estimated Average % wetted by visual observation |
|---|---|---|---|---|
| A | Water | 100 | 72.0 | 5 |
| B1 | Ethanol | 2.5 | 62.0 | 80 |
| B2 | | 7.5 | 51.4 | 90 |
| C1 | Polyethylene Glycol | 5 | 61.1 | 90 |
| C2 | 200 | 20 | 51.9 | 90 |
| D1 | Dimethyl Isosorbide | 5 | 60.9 | 80 |
| D2 | | 20 | 50.1 | 90 |
| E1 | Ethoxydiglycol | 5 | 56.8 | 80 |
| E2 | | 12.5 | 50.4 | 90 |
| F1 | Propylene Carbonate | 2.5 | 63.8 | 80 |
| F2 | | 7.5 | 49.6 | 90 |
| G1 | Propylene Glycol | 12.5 | 59.7 | 70 |
| G2 | | 30 | 50.5 | 80 |
| H | Polypropylene Glycol | 1 | 50.3 | 90 |

EXAMPLE 2

Effect of Various Solvents on Water Surface Tension

Surface tension of a fluid containing water was determined prior to and after mixing with various concentrations of various water soluble organic solvents in water. The water soluble organic solvents tested were: propylene glycol (Spectrum Chemicals, Gardena, Calif.), ethanol (Alfa Aesar, Ward Hill, Mass.), hexylene glycol (Ruger Chemicals, Linden, N.J.), ethoxydiglycol (Gattefossé USA, Paramus, N.J.), polyethylene glycol 400 (PEG 400) (Croda USA, Edison, N.J.), dimethyl isosorbide (DMI) (Croda, USA, Edison, N.J.) and glycerin (Spectrum Chemicals, Gardena, Calif.) as well as polyethylene glycol 200 NF (PEG 200) (Alfa Aesar, Ward Hill, Mass.), propylene carbonate (Spectrum Chemicals, Gardena Calif.), isopropyl alcohol (Spectrum Chemicals, Gardena Calif.), 1,3-propanediol (Spectrum Chemicals, Gardena Calif.) and polypropylene glycol (PPG-9) (Spectrum Chemicals, Gardena Calif.). The study was performed at room temperature utilizing a Kruss Surface Tensiometer, Model K20 EasyDyne (Kruss USA, Matthews, N.C.) and the results are shown in Table 4. Values for surface tension are in dynes/cm.

TABLE 4

| Concentration of Solvent % w/w in Water | Propylene Glycol USP | Ethanol (200 proof) | Hexylene Glycol NF | Ethoxy Diglycol NF | PEG 400 NF | Dimethyl Isosorbide | Glycerin USP |
|---|---|---|---|---|---|---|---|
| 0 | 71.0 | 72.0 | 71.9 | 71.8 | 72.8 | 72.8 | 72.6 |
| 1.0 | 70.8 | 67.4 | 60.1 | 66.2 | 64.2 | 66.0 | |
| 2.5 | 68.7 | 62.0 | 54.2 | 62.5 | 60.9 | 61.7 | |
| 5 | 65.9 | 55.9 | 48.9 | 56.8 | 56.6 | 52.8 | |
| 7.5 | 63.6 | 51.4 | 45.5 | 55.3 | 56.0 | 52.1 | |
| 10 | 61.7 | 47.8 | 43.0 | 53.1 | 52.5 | 47.9 | |
| 12.5 | 59.7 | 44.6 | 41.1 | 50.4 | 50.6 | 46.4 | |
| 15.0 | 58.3 | 42.2 | 39.4 | 49.7 | 49.7 | 43.5 | |
| 17.5 | 56.5 | 40.2 | 37.8 | 47.6 | 48.1 | 41.9 | |
| 20 | 55.2 | 38.0 | 36.5 | 43.2 | 46.2 | 38.6 | |
| 22.5 | 54.1 | 36.6 | 35.5 | 43.1 | 45.6 | 40.5 | |
| 25 | 52.8 | 34.9 | 34.7 | 43.8 | 45.2 | 41.7 | 69.8 |
| 30 | 50.6 | | | | | | |
| 50 | | | | | | | 68.9 |
| 75 | | | | | | | 66.4 |
| 100 | 36.1 | 22.3 | 28.6 | 32.0 | 45.0 | 39.3 | 62.0 |

| Concentration of Solvent % w/w in Water | PEG 200 | Propylene Carbonate | Isopropyl Alcohol | 1,3-Propanediol | Polypropylene Glycol (PPG-9) |
|---|---|---|---|---|---|
| 0 | 71.7 | 71.5 | 71.9 | 72.4 | 72.3 |
| 1.0 | 65.9 | 68.5 | 62.1 | 69.8 | 50.3 |
| 2.5 | 64.2 | 63.8 | 54.2 | 68.1 | 47.5 |
| 5 | 61.1 | 56.8 | 47.3 | 64.6 | 45.2 |
| 7.5 | 58.7 | 49.6 | 42.0 | 64.4 | 43.6 |
| 10 | 56.1 | 45.9 | 38.6 | 61.2 | 42.4 |
| 12.5 | 54.8 | 46.5 | 35.7 | 61.1 | 41.3 |
| 15.0 | 53.0 | 44.1 | 33.1 | 61.0 | 40.2 |
| 17.5 | 52.2 | 43.5 | 31.1 | 58.9 | 39.5 |
| 20 | 51.9 | | 29.5 | 60.4 | 38.9 |
| 22.5 | 49.9 | | 28.1 | 58.2 | 38.3 |
| 25 | 48.7 | | 27.3 | 58.3 | 37.5 |
| 100 | 45.4 | | 21.1 | | 32.5 |

As shown in Table 4, each of the organic solvents tested, with the exception of glycerin, decreased the surface tension of the water-containing fluid to less than 64 dynes/cm at room temperature. Each of ethanol, hexylene glycol, ethoxy diglycol, polyethylene glycol, propylene carbonate, isopropyl alcohol, polypropylene glycol, and dimethyl isosorbide is suitable for use in the method of the invention. The data of Table 4 indicates that the concentration suitable for the invention is 2.5% or higher for ethanol, ethoxydiglycol, polyethylene glycol 400, dimethyl isosorbide, or propylene carbonate. The suitable concentration for the invention is 1% or higher for hexylene glycol, isopropyl alcohol, or polypropylene glycol-9. Propylene glycol is shown by the data of Table 4 to be suitable at a concentration of about 7.5% or higher. Glycerin, by itself, is shown by the data of Table 4 to be not suitable for the present method at concentrations of 75% or less.

EXAMPLE 3

Wetting Benzoyl Peroxide Powder with a Fluid Comprising Propylene Glycol and Water to Facilitate the Preparation of a Stable Micronized Suspension to be Used in Manufacturing a 500 kg Batch of 2.5% Benzoyl Peroxide Topical Gel For the preparation of the suspension, a dispersing fluid containing 47.6% w/w propylene glycol (Spectrum Chemicals, Gardena, Calif.) and 52.4% w/w water was made by combining 27.5 kg of purified water and 3.75 kg of propylene glycol and agitating the combination with a propeller mixture to form a mixture. The surface tension of the fluid was measured to be less than 50 dynes/cm. While mixing, 17.3 kg of hydrous benzoyl peroxide (74.5% benzoyl peroxide) was added. Mixing continued at 1450 rpm for about 10 minutes to wet and disperse the benzoyl peroxide powder at room temperature and to obtain a benzoyl peroxide suspension.

Upon visual inspection, the suspension appeared to be smooth and free of lumps, with uniformly wetted benzoyl peroxide. This suspension was passed through a Gaulin Mill for micronization using a wet-milling method. The milling procedure proceeded efficiently and without problems (i.e., there was no mill plugging) and a stable micro-suspension was produced. This suspension was set aside for a short time before being incorporated into a gel vehicle composed of a gelling agent, water, and preservatives to provide 500 kg of a final topical dosage form, a 2.5% benzoyl peroxide gel, with the active benzoyl peroxide drug substance present as a stable micro-suspension without the use of surfactants.

The above examples show that a hydrophobic benzoyl peroxide powder is easily wetted in water containing a water soluble organic solvent that is capable of reducing the surface tension of the aqueous fluid to less than 64 dynes/cm. The wettability of the benzoyl peroxide powder increases with increased concentrations of the organic solvent and is further facilitated with mechanical agitation. If desired, the benzoyl peroxide powder that has been wetted according to the method of the invention may be effectively and safely micronized by a wet-milling or other process in order to manufacture pharmaceutical formulations containing micronized or nanosized benzoyl peroxide.

Various modifications of the above described invention will be evident to those skilled in the art. It is intended that such modifications are included within the scope of the following claims.

The invention claimed is:

1. A benzoyl peroxide suspension, the suspension consisting of micronized benzoyl peroxide in combination with an aqueous suspending fluid consisting of water and propylene glycol,
    wherein the benzoyl peroxide is at a concentration of between 1% and 30% by weight,
    wherein the concentration of the propylene glycol in the suspending fluid is sufficient to decrease the surface tension of water to less than 64 dynes/cm,
    and wherein the benzoyl peroxide suspension is characterized by minimal or no aggregation of the benzoyl peroxide.

2. The benzoyl peroxide suspension of claim 1, wherein the concentration of the propylene glycol in the suspending fluid is sufficient to decrease the surface tension of water to less than 62 dynes/cm.

3. The benzoyl peroxide suspension of claim 2, wherein the concentration of the propylene glycol in the suspending fluid is sufficient to decrease the surface tension of water to less than 61 dynes/cm.

4. The benzoyl peroxide suspension of claim 2, wherein the concentration of the propylene glycol in the suspending fluid is sufficient to decrease the surface tension of water to less than 60 dynes/cm.

5. The benzoyl peroxide suspension of claim 2, wherein the concentration of the propylene glycol in the suspending fluid is sufficient to decrease the surface tension of water to between about 55 and 60 dynes/cm.

6. The benzoyl peroxide suspension of claim 2, wherein the concentration of the propylene glycol in the suspending fluid is sufficient to decrease the surface tension of water to between about 50 and 55 dynes/cm.

7. The benzoyl peroxide suspension of claim 2, wherein the concentration of the propylene glycol in the suspending fluid is sufficient to decrease the surface tension of water to between about 50 and 62 dynes/cm.

8. The benzoyl peroxide suspension of claim 2, wherein the concentration of the propylene glycol in the suspending fluid is sufficient to decrease the surface tension of water to less than about 50 dynes/cm.

9. The benzoyl peroxide suspension of claim 1, wherein the aqueous suspending fluid consists of water and propylene glycol, wherein the benzoyl peroxide is at a concentration of between 1% and 30% by weight, and wherein the concentration of the propylene glycol in the suspending fluid is sufficient to decrease the surface tension of water to less than 50 dynes/cm.

* * * * *